United States Patent [19]

Jaenicke et al.

[11] Patent Number: 4,868,295
[45] Date of Patent: Sep. 19, 1989

[54] PROCESS FOR THE PREPARATION OF CEFODIZIME

[75] Inventors: Ottmar Jaenicke, Kelkheim; Hans Wagner, Glashütten; Manfred Worm, Wiesbaden, all of Fed. Rep. of Germany

[73] Assignee: Hoechst Aktiengesellschaft, Frankfurt am Main, Fed. Rep. of Germany

[21] Appl. No.: 936,187

[22] Filed: Dec. 1, 1986

[30] Foreign Application Priority Data

Dec. 3, 1985 [DE] Fed. Rep. of Germany ....... 3542644

[51] Int. Cl.⁴ .................. C07D 501/36; A61K 31/545
[52] U.S. Cl. .................................................. 540/227
[58] Field of Search ............................ 540/227, 317

[56] References Cited

U.S. PATENT DOCUMENTS 4,500,716 2/1985 Kinast ........................... 540/227 X
4,625,021 11/1986 Valcavi et al. ................ 540/317 X

FOREIGN PATENT DOCUMENTS 23453 2/1981 European Pat. Off. .

*Primary Examiner*—Nicholas S. Rizzo
*Attorney, Agent, or Firm*—Finnegan, Henderson, Farabow, Garrett, & Dunner

[57] ABSTRACT

A process for the preparation of cefodizime of the formula

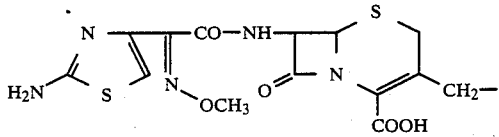

-continued

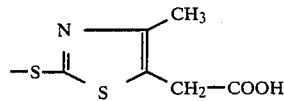

wherein
(a) a compound of the formula II (ATS)

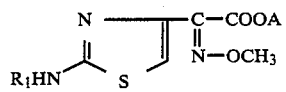

wherein $R_1$ represents hydrogen or an aminoprotective group and A represents a hydrogen atom or one equivalent of an alkali metal or alkaline earth metal, of ammonium or of an organic nitrogen base, is first reacted with a compound of the formula III

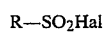

wherein R represents an optionally substituted alkyl, aryl or aralkyl radical and Hal represents a halogen atom, in an organic solvent and, if appropriate, in the presence of a base,
(b) a compound of the formula I (TACS)

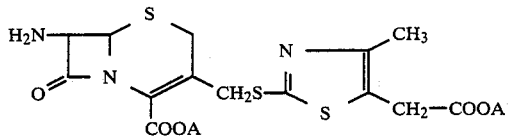

in which A has the above meaning, is reacted with a silylating agent in an organic solvent and, if appropriate, in the presence of a base, and
(c) the two products formed in (a) and (b) are reacted in their reaction solutions, and any protective group $R_1$ present in the end product of the formula I is eliminated.

14 Claims, No Drawings

PROCESS FOR THE PREPARATION OF CEFODIZIME

Cefodizime (HR 221) of the formula

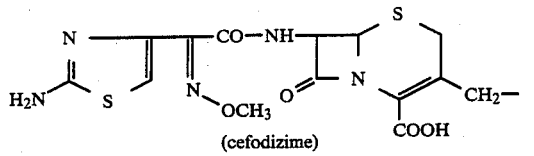
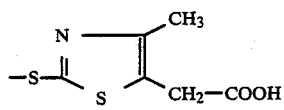
(cefodizime)

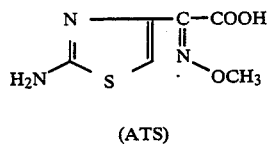

is an antibiotic whose preparation and good antibiotic activity are known from the literature. It can be obtained by reacting ATS of the formula

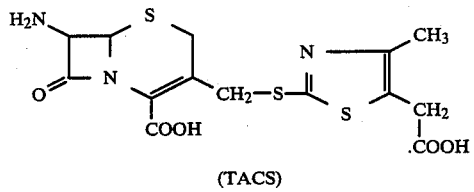

(ATS)

which is activated at the carboxyl group, with TACS of the formula (TACS)

A particularly suitable process for the preparation of cephalosporins is described in EP-A-No. 23 453. However, if this process is used for the preparation of cefodizime, about 5 to 15% of a by-product is formed in addition to the desired cefodizime. The content of by-product can be reduced by various successive purification steps, but the by-product cannot be completely removed from the cefodizime. Furthermore, these purification processes (for example chromatography or recrystallization) are expensive since they are complicated and substantially reduce the overall yield.

A number of attempts were therefore made to modify the reaction parameters with the aim of suppressing the formation of the by-product, for example variation of the molar ratios, of the temperature, of the reaction time, of the solvent, of the base, which may or may not be added, and of the activating agent, or the addition of other substances. None of these attempts were successful. It proved impossible to reduce the formation of the stated by-product.

During the investigation of further additives, it was found, surprisingly, that the formation of the by-product was virtually completely prevented by adding a silylating agent to the TACS.

The invention therefore relates to a process for the preparation of cefodizime of the formula

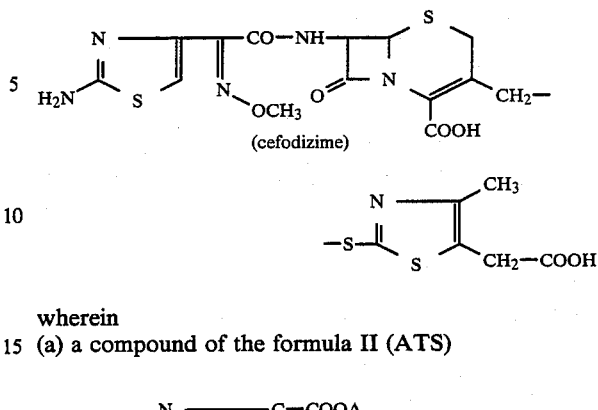
(cefodizime)

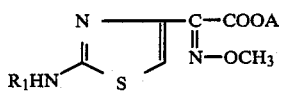

wherein
(a) a compound of the formula II (ATS)

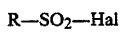

wherein $R_1$ represents hydrogen or an aminoprotective group and a represents a hydrogen atom or one equivalent of an alkali metal or alkaline earth metal, of ammonium or of an organic nitrogen base, is first reacted with a compound of the formula III R—SO$_2$—Hal wherein R represents an optionally substituted alkyl, aryl or aralkyl radical and Hal represents a halogen atom, in an organic solvent and, if appropriate, in the presence of a base,
(b) a compound of the formula I (TACS)

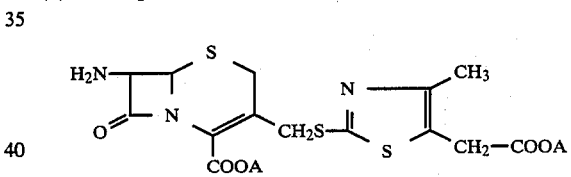

in which A has the above meaning, is reacted with a silylating agent in an organic solvent and, if appropriate, in the presence of a base, and
(c) the two products formed in (a) and (b) are reacted in their reaction solutions, and any protective group $R_1$ present in the end product of the formula I is eliminated.

In addition to representing hydrogen or ammonium, A can furthermore represent one equivalent of an alkali metal, such as, for example, sodium or potassium, of an alkaline earth metal, such as, for example, calcium or magnesium, or of an organic nitrogen base, such as, for example, diethyl-, trimethyl-, triethyl-, methyl-, propyl-, N,N-dimethylethanol- or ethanolamine.

Suitable protective groups $R_1$ are those described as aminoprotective groups in cephalosporin chemistry or peptide chemistry, for example those mentioned in EP-A-No. 23 453, page 3, lines 43–63. Compounds in which $R_1$ represents hydrogen are preferably used according to the invention. Because protection of the amino group is not obligatory, two reaction stages (protection and elimination) can be dispensed with, leading to a further increase in yield.

Suitable compounds of the formula III are all those which are described in the literature as being suitable for reaction with a carboxylic acid, such as, for example, methanesulfonyl chloride or tosyl chloride, an activated carboxylic acid radical —COOSO$_2$R probably being formed. Because they possess good reactivity and are readily obtainable, compounds such as p-tosyl chloride or phenylsulfonyl chloride are preferred. Compounds of the formula III in which Hal represents chlorine are also preferred.

The reaction between the compound of the formula II and a compound of the formula III can be carried out in an anhydrous organic solvent, such as, for example, acetone, ethyl acetate, tetrahydrofuran, acetonitrile, carbon tetrachloride, methylene chloride, toluene, dioxane, isopropyl ether, N-methylpyrrolidone or dimethylformamide, but preferably in dimethylacetamide, at temperatures between about −30° and 0° C., preferably between −10° and −15° C.

If the compound of the formula II is employed in the form of the free acid (A=hydrogen), it is advantageous to add a base, preferably an organic nitrogen base, such as, for example, triethylamine, N,N-dimethylaniline, tributylamine, N-methylmorpholine, pyridine or picoline, or, for example, sodium carbonate, potassium carbonate, sodium bicarbonate, or potassium bicarbonate, in particular triethylamine. The addition of the base can be dispensed with if the carboxylic acid of the formula II is employed in the form of one of the abovementioned salts.

The further reaction is then carried out as follows: the compound of the formula I (TACS), in an anhydrous organic solvent, such as, for example, methylene chloride, dimethylacetamide, methyl tert.-butyl ether, methyl isobutyl ketone, butyl acetate or amyl acetate, in particular methylene chloride or methyl tert.-butyl ether, is reacted with about 3 mol equivalents of a silylating agent, preferably with trimethylchlorosilane, in the presence of—based on the silylating agent—about a stoichiometric amount of an organic nitrogen base, in particular triethylamine, and the product is then brought to reaction with the carboxylic acid of the formula II which has been activated by reaction with a compound of the formula III.

Instead of trimethylchlorosilane, it is also possible to employ other silylating agents, such as, for example, bis-trimethylsilylacetamide, dichlorodimethylsilane, trichloromethylsilane or N,N′-bis-trimethylsilylurea, bistrimethylsilylacetamide being preferred among these further silylating agents. A small excess of the silylating agent over and above the 3 mol equivalents has no adverse effect on the reaction.

When bis-trimethylsilylacetamide or N,N′-bis-trimethylsilylurea is used, it is not necessary to add a base during the silylation since in this case no hydrochloric acid, which would have to be bound, does not occur.

The silylation of the compound of the formula I is carried out at temperatures between about 20° and 25° C. The temperature can also be allowed to increase to, for example, about 40° C. (boiling point of methylene chloride).

The activated ATS is advantageously combined with the silylated TACS as follows: the solution of the activated ATS is added to the solution of the silylated TACS at temperatures between about −20° and 0° C., preferably between −10° and −12° C., sufficiently slowly to permit the resulting heat of reaction to be easily conducted away, for example over a period of ¼ to 2 hours.

The reaction mixture is stirred for a short time and then worked up in a manner known per se. Thus, for example, it can be poured into water the pH value of which is kept at about 6.0–7.5 by adding, for example, an organic nitrogen base, in particular triethylamine. After phase separation, the organic phase can then be extracted again with water in which sodium acetate has been dissolved. From the combined aqueous phases, which, if necessary, may furthermore be clarified with, for example, active carbon, the cefodizime can then be precipitated as the free acid by adjusting the pH value to about 2.8, by adding a mineral acid, for example, sulfuric acid.

Where the carboxylic acid of the formula II has been employed with an aminoprotective group $R_1$, elimination of this radical in a manner described in the literature must be carried out prior to working up.

After drying at a slightly elevated temperature and in vacuo, the cefodizime acid is obtained in very pure form.

In addition to the abovementioned, unexpected reduction of the content of the by-product to well below 1%, it should also be pointed out that, for example in the illustrative examples 8 to 12 of EP-A-No. 23 453 mentioned above, reaction temperatures between −70° and −72° C. are employed in the acylation. In contrast, it is possible to carry out the reaction according to the invention at temperatures of about −20° to 0° C. without this resulting in a deterioration in quality or yield. This fact is of considerable importance for the industrial production of cefodizime, since it implies shorter occupation times and a smaller cooling capacity.

EXAMPLE 1

Stage 1

17.5 kg (87.1 moles) of ATS in 52 kg of dimethylacetamide are converted with 8.95 kg (88.6 moles) of triethylamine to the ammonium salt at a temperature of 20° to 22° C., while stirring for 30 minutes.

12.9 kg (68.0 moles) of p-toluenesulfonyl chloride are dissolved in 13.2 kg of dimethylacetamide in the course of 30 minutes at 20°–25° C., and this solution is allowed to run, at −10° C. to −14° C., into the suspension of the triethylammonium salt of ATS in the course of 30 minutes, and stirring is continued for a further 2.5 hours.

Stage 2

23.7 kg (59.0 moles) of TACS are suspended in 212 kg of methylene chloride, 19.7 kg (181.0 moles) of trimethylchlorosilane are allowed to run in at 20°–25° C., and 18.2 kg (180.0 moles) of triethylamine are added in the course of 30 minutes at a temperature of 20°–41° C. (reflux temperature of the methylene chloride).

When the addition is complete, the solution is cooled very rapidly to −15° C., and the solution of the activated ATS obtained as described in stage 1 is added in the course of 30 minutes at −10° to −12° C. Stirring is continued for a further 5 minutes, after which the reaction mixture is allowed to run into a mixture of 143 liters of water and 19.3 kg of triethylamine in the course of 5 to 10 minutes, the pH value being kept at between 6 and 7.5. After phase separation, the methylene chloride phase is again extracted with 70 liters of water in which 2.2 kg of sodium acetate. 3 $H_2O$ have been dissolved, the combined aqueous phases are clarified with 1.2 kg of active carbon and 1.2 kg of dicalite, and the cefodizime is then precipitated in the form of the free acid from these phases by adding 18% strength sulfuric acid until a pH value of 2.8 is reached. After the product has been filtered off and dried at 40° C. and under 100 mm Hg, 30.6 kg of cefodizime are obtained in a purity of 96–97% by area according to HPLC analysis.

EXAMPLE 2

Stage 1 corresponds to the procedure stated in Example 1.

Stage 2

23.7 kg (59.0 moles) of TACS are suspended in 212 kg of methylene chloride, and 36.0 kg (177.0 moles) of bis-trimethylsilylactamide are added. Stirring is carried out for 30 minutes at 20°–25° C., the clear solution is cooled to −15° C., and the solution of the activated ATS obtained as described in stage 1 is added in the course of 30 minutes at −10° to −12° C. After stirring has been carried out for 5 minutes, the reaction mixture is allowed to run into 143 liters of water in the course of 5 to 10 minutes, and at the same time the pH value is kept between pH 6.0 and 7.5 with triethylamine. After phase separation, the organic phase is again extracted with 70 kg of water which contains 2.2 kg of sodium acetate. 3 $H_2O$. The combined, aqueous phases are clarified with 1.2 kg of active carbon and 1.2 kg of dicalite, and the product is precipitated by adding 18% strength sulfuric acid until a pH value of 2.8 is reached. After the product has been filtered off and dried at 40° C. and under 100 mm Hg, 30.0 kg of cefodizime are obtained in the form of the free acid, in a purity of 95 to 97% by area according to HPLC analysis.

We claim:

1. A process for the preparation of cefodizime of the formula

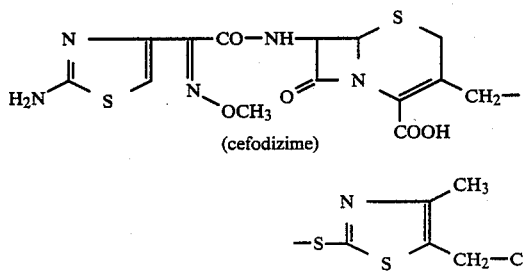
(cefodizime)

wherein
(a) a compound of the formula II (ATS)

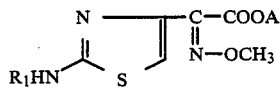

wherein $R_1$ represents hydrogen or an aminoprotective group and A represents a hydrogen atom or one equivalent of an alkali metal or alkaline earth metal, of ammonium or of an organic nitrogen base, is first reacted with a compound of the formula III

wherein R represents an optionally substituted alkyl, aryl or aralkyl radical and Hal represents a halogen atom, in an organic solvent and, if appropriate, in the presence of a base, (b) a compound of the formula I (TACS)

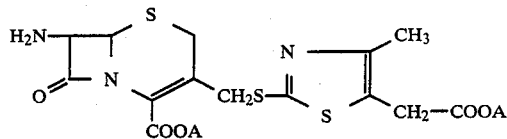

in which A has the above meaning, is reacted with a silylating agent in an organic solvent and, if appropriate, in the presence of a base, and (c) the two products formed in (a) and (b) are reacted in their reaction solutions, and any protective group $R_1$ present in the end product of the formula I is eliminated.

2. The process as claimed in claim 1, wherein, in the compound of the formula III, R represents p-tosyl or phenyl and Hal represents chlorine.

3. The process as claimed in claim 2, wherein R represents p-tosyl.

4. The process as claimed in claim 1, wherein, in the compound of the formula II (ATS), $R_1$ and A represent hydrogen.

5. The process as claimed in claim 1, wherein the solvent employed in process stage (a) is acetone, dimethylacetamide, ethyl acetate, tetrahydrofuran, acetonitrile, carbon tetrachloride, methylene chloride, toluene, dioxane, isopropyl ether, n-methylpyrrolidone or dimethylformamide.

6. The process as claimed in claim 5, wherein the solvent is dimethylacetamide.

7. The process as claimed in claim 1, wherein the silylating agent is trimethylchlorosilane, dichlorodimethylsilane, trichloromethylsilane, bis-trimethylsilylacetamide or N,N'-bistrimethylsilylurea.

8. The process as claimed in claim 7, wherein the silylating agent is trimethylchlorosilane.

9. The process as claimed in claim 7, wherein 3 mol equivalents, based on the TACS, of the silylating agent are employed.

10. The process as claimed in claim 1, wherein the employed in process stage (b) is methylene chloride, dimethylacetamide, methyl tert.-buty. ether, methyl isobutyl ketone, butyl acetate or amyl acetate.

11. The process as claimed in claim 9, wherein the solvent is methylene chloride or methyl tert.-butyl ether.

12. The process as claimed in claim 1, wherein the base which, if appropriate, is added during the individual process stages is triethylamine.

13. The process as claimed in claim 1, wherein the reaction of process stage (a) is carried out at temperatures between about −30° and 0° C.

14. The process as claimed in claim 1, wherein the reaction of process stage (b) is carried out at temperatures between about −20° and 0° C.

* * * * *

UNITED STATES PATENT AND TRADEMARK OFFICE
CERTIFICATE OF CORRECTION

PATENT NO. : 4,868,295
DATED : September 19, 1989
INVENTOR(S) : Ottmar Jaenicke et al.

It is certified that error appears in the above-identified patent and that said Letters Patent is hereby corrected as shown below:

Claim 10, Column 6, lines 46 and 47, change "the employed" to --the solvent employed--.

In the Abstract, Column 2, change "$R-SO_2Hal$" to --$R-SO_2-Hal$--.

Signed and Sealed this

Second Day of July, 1991

Attest:

HARRY F. MANBECK, JR.

*Attesting Officer*  Commissioner of Patents and Trademarks